United States Patent [19]

Hakim et al.

[11] Patent Number: 4,608,992

[45] Date of Patent: Sep. 2, 1986

[54] EXTERNAL MAGNETIC DETECTION OF PHYSIOPATHOLOGICAL AND OTHER PARAMETERS

[76] Inventors: Salomon Hakim, Carrera 13, N. 48-26, Bogota, Colombia; Carlos A. Hakim, 3400 Galt Ocean Dr., Apt. 1702 South, Fort Lauderdale, Fla. 33308

[21] Appl. No.: 524,367

[22] Filed: Aug. 18, 1983

[51] Int. Cl.$^4$ .............................................. A61B 5/05
[52] U.S. Cl. ..................................... 128/654; 128/748
[58] Field of Search ................................ 128/653–654, 128/748, 655–658; 73/722, 728; 324/246, 244, 251, 259–261

[56] References Cited

U.S. PATENT DOCUMENTS

| | | | |
|---|---|---|---|
| 3,013,206 | 12/1961 | Youngquist et al. | 324/38 |
| 3,853,117 | 12/1974 | Murr | 128/748 X |
| 4,026,276 | 5/1977 | Chubbuck | 128/748 |
| 4,062,354 | 12/1977 | Taylor et al. | 128/748 X |
| 4,141,348 | 2/1979 | Hittman | 128/748 |
| 4,147,161 | 4/1979 | Ikebe et al. | 128/748 |
| 4,317,078 | 2/1982 | Weed et al. | 128/653 X |
| 4,340,038 | 7/1982 | McKean | 128/748 X |
| 4,378,809 | 4/1983 | Cosman | 128/748 |
| 4,431,005 | 2/1984 | McCormick | 128/653 X |

OTHER PUBLICATIONS

Hakim, S. and Adams, R. D., "The Special Clinical Problem of Symptomatic Hydrocephalus with Normal Cerebrospinal Fluid Pressure: Observations on Cerebrospinal Fluid Hydrodynamics", *J. Neurol. Sci.*, 1965, 2:307–327.

Hakim, S. "Some Observations on C.S.F. Pressure. Hydrocephalic Syndrome in Adults with Normal C.S.F. Pressure (Recognition of a New Syndrome).", Javeriana University School of Medicine, Bogota, Colombia, 1964, Thesis No. 957.

Lundberg, N., "Continuous Recording and Control of Ventricular Fluid Pressure in Neurosurgical Practice", *Acta Psychiat. Neuro. Scand.*, Suppl. 36, 1960.

Cosman, E. R.; Zervas, N. T.; Chapman, P. H., "A Telemetric Pressure Sensor for Ventricular Shunt Systems", *Surgical Neurology*, 11 pp. 287–294, 1979.

Cosman, E. R., "A Pressure–Balanced Radio Telemetry System for the Measurement of Intracranial Pressure" *J. Neurosurgery*, 47, pp. 899–911, 1977.

Viernstein, Lawrence and Gucer, Gunduz, "Clinical Use of Intracranial Pressure Monitor", Apr. 1979.

*Primary Examiner*—Kyle L. Howell
*Assistant Examiner*—Angela D. Sykes
*Attorney, Agent, or Firm*—G. Roger Lee

[57] ABSTRACT

A technique for transmitting from within the body information concerning an internal parameter (e.g., a measurement of a physiopathological parameter or a parameter generated by an implanted pacemaker), without physical connections to the implanted device, without an externally applied or internally generated electromagnetic field, and without implantation of radioactive material. The implanted device generates a magnetic field having an orientation influenced by changes in the internal parameter. The field is generated by one or more permanent magnets in the implanted device. The orientation of the field is detected externally using a viewer that provides a display indicative of the orientation. The display may provide an image of the magnetic field (e.g., a compass needle or magnetometer) that aligns itself with the field in a known manner. The magnetic field can be generated by a rotatable element on which are carried one or more permanent magnets (e.g., a disk of a magnetic alloy such as samarium cobalt on which has been impressed one or more magnetic regions). In some embodiments the image seen in the viewer is in the form of a pointer (e.g., an arrow) and is provided by implanted magnets that have a north/south boundary of the same shape. If the internal parameter is a fluid pressure, the implanted device may include a diaphragm manometer with a rotatable drum (e.g., rotated by levers connected to the diaphragm and arranged to pull a thread wrapped around the drum) on which is mounted the previously mentioned disk with impressed magnetic regions.

61 Claims, 17 Drawing Figures

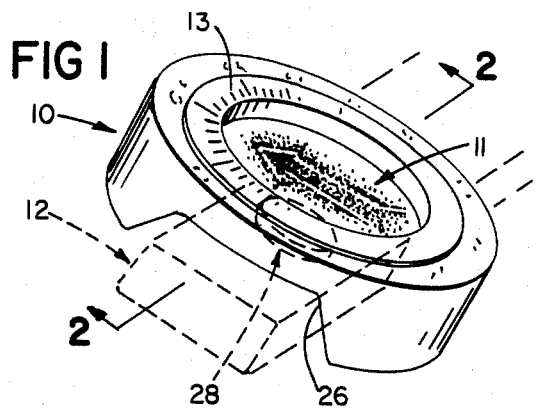
FIG 1
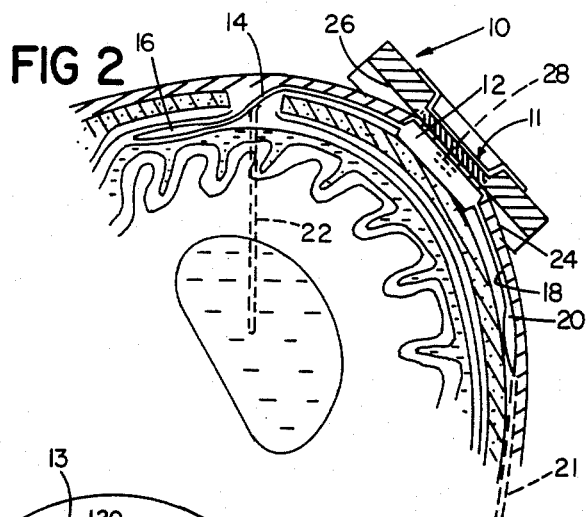
FIG 2
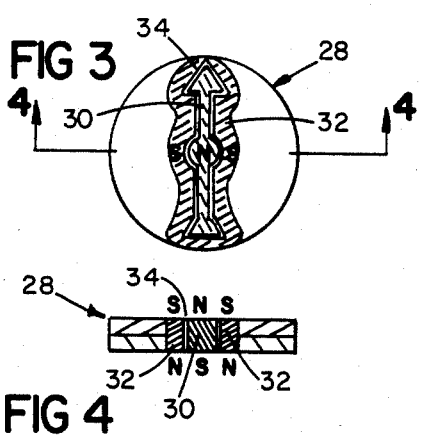
FIG 3
FIG 4
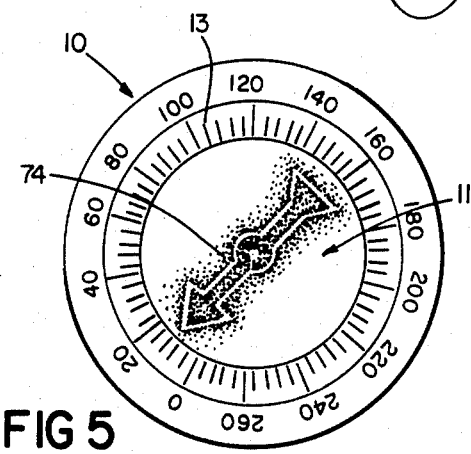
FIG 5
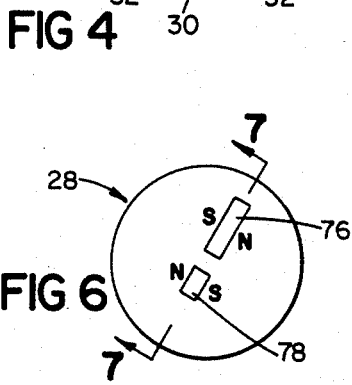
FIG 6
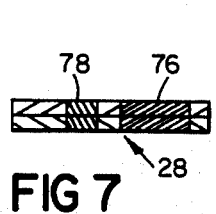
FIG 7
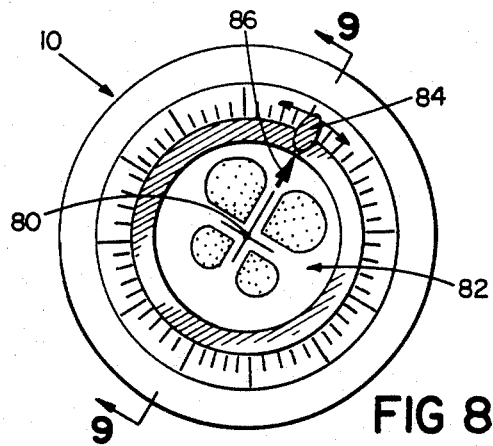
FIG 8
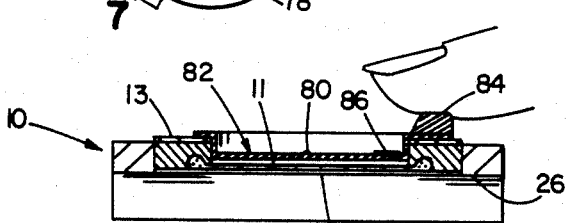
FIG 9
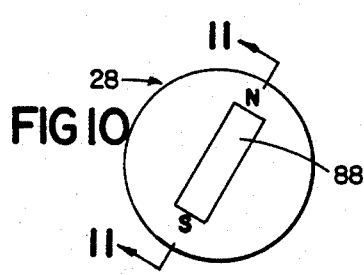
FIG 10
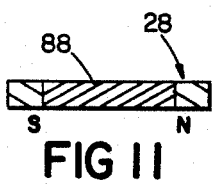
FIG 11
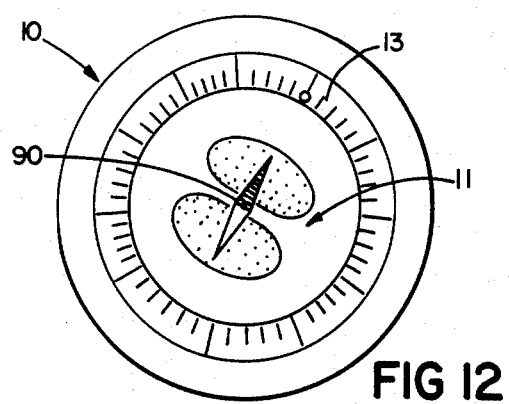
FIG 12

EXTERNAL MAGNETIC DETECTION OF PHYSIOPATHOLOGICAL AND OTHER PARAMETERS

BACKGROUND OF THE INNVENTION

This invention relates to measurement of physiopathalogical parameters, for example, body fluid pressures.

On physiopathological parameter for which there has been much interest in developing measurement techniques is intracranial pressure. Interest in measuring that parameter has become especially intense since the discovery by applicant Salomon Hakim in the mid 1960's of the normal pressure hydrocephalus syndrome. (Hakim, S.: "Some Observations on C.S.F. Pressure. Hydrocephalic Syndrome in Adults with Normal C.S.F. Pressure (Recognition of a New Syndrome)." Javeriana University School of Medicine, Bogota, Colombia. 1964, Thesis No. 957. Hakim, S., Adams, R. D. "The special clinical problem of symptomatic hydrocephalus with normal cerebrospinal fluid pressure: Observations on cerebrospinal fluid hydrodynamics.", *J. Neurol. Sci.* 1965, 2:307-327.)

A very early technique for measuring intracranial pressure, developed by James B. Ayer at the Massachusetts General Hospital, relied on insertion of a needle into the lumbar subarachnoid space and connection of the needle via a catheter to an externally located open bore manometer. Subsequent improvements reported in Guillaume, J. and Janny, P., "Manometrique Intracranienne Continue", *Rev. Neurol.* 84, 131-142 (1951) and Lundberg, N., "Continuous Recording and Control of Ventricular Fluid Pressure in Neurosurgical Practice", *Acta Psychiat. Neuro. Scand.*, Suppl. 36 (1960) replaced the open bore manometer with a strain gauge instrument, also located externally of the patient and connected via a catheter. A further improvement was to implant a small strain gauge in the patient and pass wires through the scalp.

All of these techniques shared the difficulty that a physical connection was necessary through the skin, resulting in a serious risk of infection, a likelihood of discomfort for the patient, and a probable need subsequently for sugical removal of the implanted device.

to overcome those difficulties there have been efforts at developing sensor devices that can be implanted indefinitely in the body without any physical connections such as catheters or wires. Exemplary of those efforts is the work done at Johns Hopkins University in the mid to late 1970's. Described in Chubbuck U.S. Pat. No. 4,026,276 and Viernstein, L. and Gucer, G., "Clinical Use of Intracranial Pressure Monitor: Final Report" (April 1979), a technique was developed in which a passive resonant circuit having a resonant frequency influenced by the intracranial pressure is implanted in a hole cut through the skull. Pressure measurements are made by imposing an external electromagnetic field of variable frequency and observing the frequency at which the implanted resonant circuit absorbs energy.

Another technique on which substantial work has been done is the implantation of a device in which a radioactive material is forced from a lead chamber into an adjoining chamber to a degree dependent upon the intracranial pressure being measured. External measurement is made using a radiation detector.

Another known technique generally for measuring physiopathological parameters is to implant an active electronic circuit in the body, one capable of sending electromagnetic transmissions to an outside receiver, and to modulate the transmitted signal with information relating to the measurement.

A very recently-developed technique by Cosman described in Cosman, E. R.; Zervas, N. T.; Chapman, P. H.; "A Telemetric Pressure Sensor for Ventricular Shunt Systems", *Surgical Neurology*, 11, 287-294, 1979, implants a coil and movable magnetic core in an aperture in the skull, with the core being connected to a diaphragm whose interior surface is exposed to the patient's intracranial pressure. Pressure measurements are made by applying a balancing pressure to the outside of the diaphragm sufficient to move the magnetic core to a reference position within the implanted coil and then reading a gauge indicating the amount of external pressure required (core position is detected by application of an external electromagnetic field).

SUMMARY OF THE INVENTION

We have discovered a new technique for transmitting to the outside of the body measurements of physiopathological parameters, one that not only avoids physical connections to the implanted sensor device but that can function without an externally applied or internally generated electromagnetic field, and without implantation of radioactive material. The invention can be applied to measuring all types of physiopathological parameters (depending on the measurand sensed by the sensing element), intracranial pressure being only one example. It provides accurate measurements that can be made rapidly, without discomfort to the patient, and with greatly reduced risk of infection. Moreover, it is uncomplicated and reliable. And because the implanted device and external detector are purely mechanical in many embodiments of the invention, electrical drift errors can be avoided (errors that typically require invasive spinal tap measurements to recalibrate).

In general the invention features implanting a device that generates a magnetic field having an orientation influenced by changes in the physiopathological parameter being measured and externally detecting the orientation of that field. In preferred embodiments, the field is generated by one or more permanent magnets in the implanted device; the orientation of the field is detected externally using a viewer that provides a display indicative of the orientation; the display either provides directly an image of the magnetic field (e.g., using a suspension of weakly-ferromagnetic crystals) or it consists of a magnetic element (e.g., a compass needle or magnetometer) that aligns itself with the field in a known manner; the magnetic field is generated by a rotatable element on which are carried one or more permanent magnets (e.g., a disk of a magnetic alloy such as samarium cobalt on which has been impressed one or more magnetic regions); the image projected in the viewer by the field is used to align a pointer (e.g., cross hairs with one hair forming a pointer) with the center of rotation of the magnetic field; the image formed in the viewer is provided by shaping the magnets so that the boundary between adjoining north and south polarity regions is in the form of the desired image; in some embodiments the image is itself in the form of a pointer (e.g., an arrow) and is provided by implanted magnets that have a north/south boundary of the same form; the strength of adjoining north and south polarity regions is equalized so that the projected image remains generally undistorted at varying viewing distances; the projected image has an asymmetry (e.g., an arrow with a recognizable tip and tail) that permits detection of the angular orientation of the magnetic field through a full 360° rotation; if the physiopathological parameter being measured is a fluid pressure, the implanted device includes a diaphragm manometer with a rotatable drum (e.g., rotated by levers connected to the diaphragm and arranged to pull a thread wrapped around the drum) on which is mounted the previously mentioned disk with impressed magnetic regions.

Other advantages and features of the invention will be apparent from the following description of preferred embodiments and from the claims.

BRIEF DESCRIPTION OF THE DRAWINGS

FIG. 1 is a perspective, somewhat diagrammatic, view of a first preferred embodiment of the invention.

FIG. 2 is a cross-sectional view taken along 2—2 of FIG. 1, showing the implanted manometer and external ferromagnetic crystal viewer of said first embodiment.

FIG. 3 is a plan view of the magnetic disk within the manometer of said first embodiment.

FIG. 4 is a cross-sectional view taken along 4—4 in FIG. 3.

FIG. 5 is a view showing the ferromagnetic crystal viewer and projected image of said first embodiment.

FIG. 6 is a plan view of the magnetic disk within the manometer of a second preferred embodiment.

FIG. 7 is a cross-sectional view taken along 7—7 in FIG. 6.

FIG. 8 is a view showing the ferromagnetic crystal viewer and image of said second embodiment.

FIG. 9 is a cross-sectional view taken at 9—9 in FIG. 8, showing the rotatable plastic insert mounted on the ferromagnetic crystal viewer of said second embodiment.

FIG. 10 is a plan view of the magnetic disk within the manometer of a third preferred embodiment.

FIG. 11 is a cross-sectional view taken at 11—11 in FIG. 10.

FIG. 12 is a view showing the ferromagnetic crystal viewer and image of said third embodiment.

DESCRIPTION OF THE PREFERRED EMBODIMENTS

Figure 13:
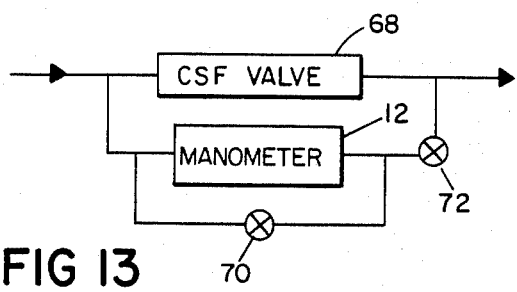
FIG. 13 is a schematic view showing the manometer installed in parallel with a cerebrospinal fluid shunt valve.

There is shown in FIGS. 1 and 2 a ferromagnetic crystal viewer 10 positioned over an implanted manometer 12 (shown in dashed lines). Tube 14 connects the manometer to an isotonic saline solution filled bladder 16 positioned to serve as a subdural pressure sensor. Tube 18 connects the manometer to another saline solution filled bladder 20 positioned between the scalp and the skull so as to provide an atmospheric pressure reference. An alternative means of providing an atmospheric pressure reference is to connect tube 18 to the right atrium by means of catheter 21. Shown in dashed lines in FIG. 2 is catheter 22, used when it is desired to measure the cerebrospinal fluid pressure in the ventricle. Manometer 12 forms a palpable protrusion 24 on the surface of the skin over which mating recess 26 of viewer 10 fits.

Viewer 10 contains a suspension of weakly-ferromagnetic crystals of the type conventionally used in viewers for inspecting magnetic tapes, as described in Youngquist et al. U.S. Pat. No. 3,013,206. The viewer has a transparent (glass or plastic) top surface 11 and a surrounding annular graded scale 13, which is rotatable relative to the viewer housing to allow zeroing. In its bottom surface there is provided a recess 26 shaped to mate with the skin protrusion 24 formed by implantation of manometer 12. The viewer includes a venting screw (not shown) for venting the cavity containing the suspension whenever a change in the ambient pressure occurs (e.g., as the result of travel to a different altitude). The suspension is supported above a thin (0.005 inch thick) nickel-plated copper bottom panel 15 (FIG. 9), which resists corrosion and provides a shiny upper surface for enhanced viewing.

Figure 14:
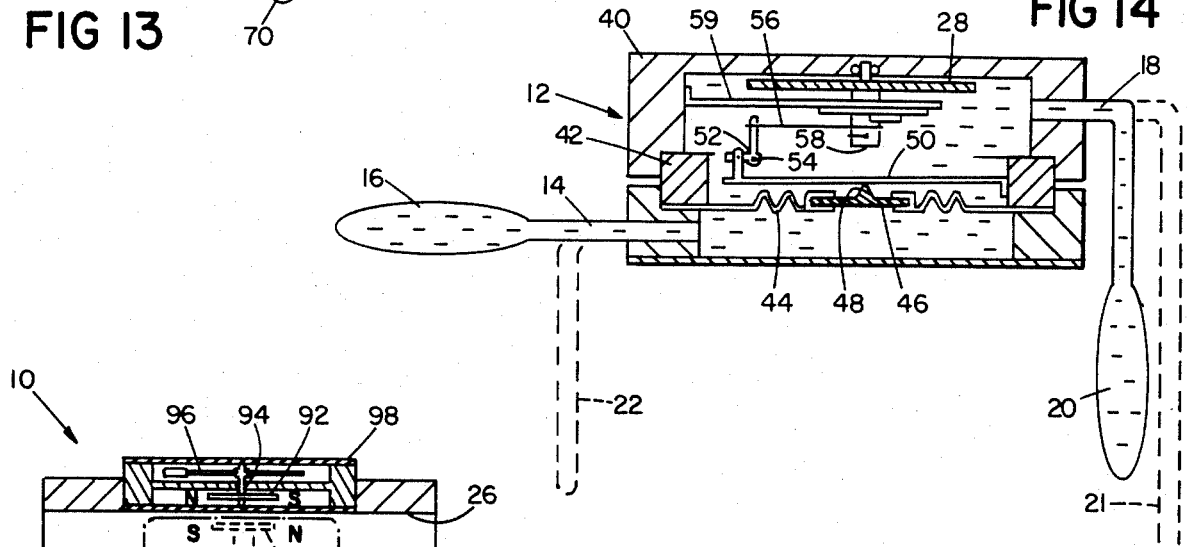
FIG. 14 is a cross-sectional view of the presently most preferred embodiment of the implanted manometer.

Turning to FIGS. 3, 4 and 14 there is shown the internal mechanism of the manometer 12. It contains a magnetic disk 28 (samarium cobalt) that rotates in response to changes in the pressure difference between sensor bladder 16 and reference bladder 20.

Disk 28 has impressed on it permanent magnetic regions 30, 32 spaced slightly apart to form a boundary 34 having an arrow shape. (The two regions are formed on disk 28 using conventional procedures used for forming the magnetic disks used in small stepping motors. Specifically, the disk is placed between powerful electromagnets having the same general shapes as the regions to be impressed.) Region 30 has its north polarity on the upper surface of disk 38, and its south polarity on the lower surface (FIG. 4). Region 32 has the opposite polarity: south polarity on the top surface and north polarity on the bottom. There is thus a change in polarity all along boundary 34 between the regions. The size of outer region 32 is selected to give it roughly equal magnetic strength to that of region 30 so that the image projected by boundary 34 will remain generally undistorted at varying separations between viewer 10 and manometer 12.

Manometer 12 shown in FIG. 14 has body 40 (injection molded polyethersulfone plastic) consisting of two halves between which is clamped stainless steel ring 42. Tubes 14, 18 are connected to the housing by stainless steel tubes (not shown) inserted into the walls of the housing. Supported between the two halves of the housing in diaphragm 44 (silicone rubber), which has secured (captured in an annular groove) to its center a circular plate 46 (stainless steel) with central fulcrum protrusion 48. The protrusion bears against lever arm 50, which drives two-arm crank 52 (pivoted at 54), which, in turn, pulls thread 56 (silk or nylon), causing rotation of drum 58, to which magnetic disk 38 is attached. A spiral-wound torsion spring 59 resists rotation of the drum to maintain tension on thread 56. An adjustment screw (not shown) is used to adjust the torsion on the drum and thereby the zero position of the manometer. Drum 58 is supported at one end in the housing and at the other by a support not shown. Lever arm 50 and two-arm crank 52 provide a large mechanical amplification of the movement of plate 46. One full revolution of drum 58 occurs for that movement of plate 46 corresponding to a full scale change in pressure of the range being measured.

Figure 15:
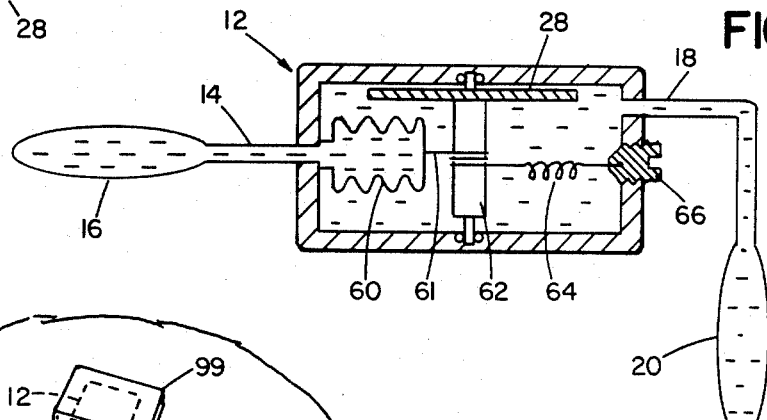
FIG. 15 is a cross-sectional view of another preferred embodiment of the implanted manometer.

Another embodiment of the manometer is shown in FIG. 15. The diaphragm of FIG. 14 is replaced by bellows 60, which pulls thread 61 wound around drum 62 and held in tension by helical spring 64. Screw 66 is used to adjust the zero position of the manometer.

Manometer 12 is surgically implanted in a patient following conventional procedures similar to those used for implanting cerebrospinal fluid shunt valves.

An alternative application for the manometer, different than the one shown in FIG. 2, is to measure the pressure difference across a cerebrospinal fluid shunt valve. In this application the manometer is installed as shown in the schematic of FIG. 13, in parallel with the shunt valve 68. When the manometer is inoperative, valve 70 is open and valve 72 closed, thereby providing a zero pressure difference across the manometer. To make a pressure measurement, valve 70 is first closed, and then valve 72 is opened. Valves 70, 72 are preferably implanted and provided as one unit operated by application of finger pressure at one location on the skin surface.

Measurement of the intracranial pressure is made by placing viewer 10 over skin protrusion 24 at the location of implanted manometer 12. Reasonably accurate initial positioning is achieved in this manner. (As it may be possible to place the viewer over the protrusion in two, or possibly more, orientations, it may be preferable in some applications to provide some type of indicia on the viewer to assist the user in choosing the correct orientation; e.g., the proper orientation of the viewer with respect to inlet tube 14 and outlet tube 18 of the manometer.)

Once placed over manometer 11, the viewer provides an image 74 in the suspension of ferromagnetic crystals (FIG. 5) of an arrow corresponding to the shape of boundary 34 between magnetic regions 30, 32. The arrow-shape image appears as a white line caused by the absence of the ferromagnetic crystals, which tend to collect nearest the poles of the magnetic regions. The whiteness of the line is due to the highly reflective upper surface of bottom panel 15. The size of the arrow-shape image is dependent on the separation of the viewer from the magnetic regions in the implanted manometer. Preferably the viewer is sized so that when placed firmly over skin protrusion 24 the arrow-shape image nearly fills the field of view. In that event centering of the arrow is simplified. The circular shape provided at the center of the arrow is also helpful for centering purposes. Centering is desirable for enhancing accuracy of readings, which are made by simply noting the pressure pointed to on scale 13.

A second embodiment of the invention is shown in FIGS. 6–9. In this embodiment the layout of magnetic regions on the manometer disk 28 is different. Two generally rectangular magnetic regions 76, 78 (shown in plan view in FIG. 6 and cross section in FIG. 7) are spaced apart slightly. Both regions 76 and 78 have exposed on the upper surface of the disk 38 both north and south poles, as shown in FIG. 6. This arrangement of magnetic regions produces the image shown in FIG. 8 in the ferromagnetic crystal viewer 10. An assymetric four-lobe pattern appears, and is used to align cross hairs 80, which are aligned so that the intersection coincides with the center of the four-lobe pattern, which in turn corresponds to the center of rotation of disk 28.

The cross hairs are imprinted on the surface of a transparent rotatable plastic ring 82 inserted inside the viewer and resting on transparent surface 11 as shown in FIG. 9. The orientation of the cross hairs 80 can be aligned with the assymetric four-lobe pattern by holding the viewer 10 in one hand while using the other hand to rotate the plastic ring 82. A small protrusion 84 connected to the plastic ring 82 as shown in FIG. 9 facilitates the rotation and alignment of the cross hairs 80. One of the imprinted cross hairs 80 is extended in the shape of a pointer 86 as shown in FIG. 8. The pressure reading is taken from the graded scale as indicated by the pointer 86. The narrowness of the pointer 86 helps to make faster and more accurate pressure readings from the graded scale.

A third embodiment of the invention is shown in FIGS. 10–12. A single magnetic region 88 is provided on the magnetic disk 28 in the manometer. The image projected from this magnetic region onto viewer 10 is the dipolar pattern shown in FIG. 12. Mounted on viewer 10 is a compass needle 90. When the center of the viewer display is positioned over the center of the dipolar pattern the magnetic attraction of magetic region 88 will cause the compass needle 90 to automatically align with the implanted magnetic region. Accurate alignment of the viewer over the magnetic disk of the manometer may be attained by matching the actual crystal pattern with a nominal pattern (e.g., one imprinted in a color on the surface of the display). Accurate alignment is necessary because a small misalignment of the center of compass needle 90 with the center of magnetic region 88 on disk 28 will cause a large change in the direction in which the compass needle points. Pressure measurements are made by reading from scale 13 the pressure to which a designated end of the compass needle points.

Figure 16:
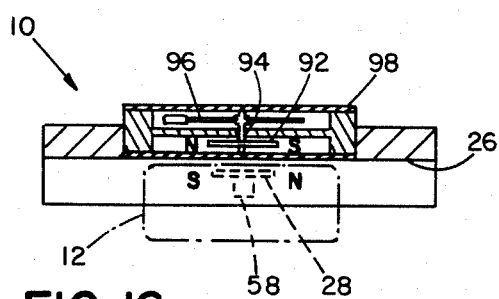
FIG. 16 is a cross-sectional view of the external viewer of a fourth embodiment.

A fourth embodiment is shown in FIG. 16. This embodiment is intended to be used in conjunction with the single magnetic region embodiment of FIGS. 10 and 11. The ferromagnetic crystal viewer has been eliminated, and in its place is a small permanent magnet 92 (similar to a small compass needle) mounted on the same rotatable shaft 94 (supported in ruby bearings) as a much longer pointer 96, which is used in conjunction with graded scale 98 to read measurements. This arrangement provides a magnet of a size that better approximates the size of the implanted magnetic region while also providing a large pointer, all of which improves measurement accuracy.

OTHER EMBODIMENTS

Figure 17:
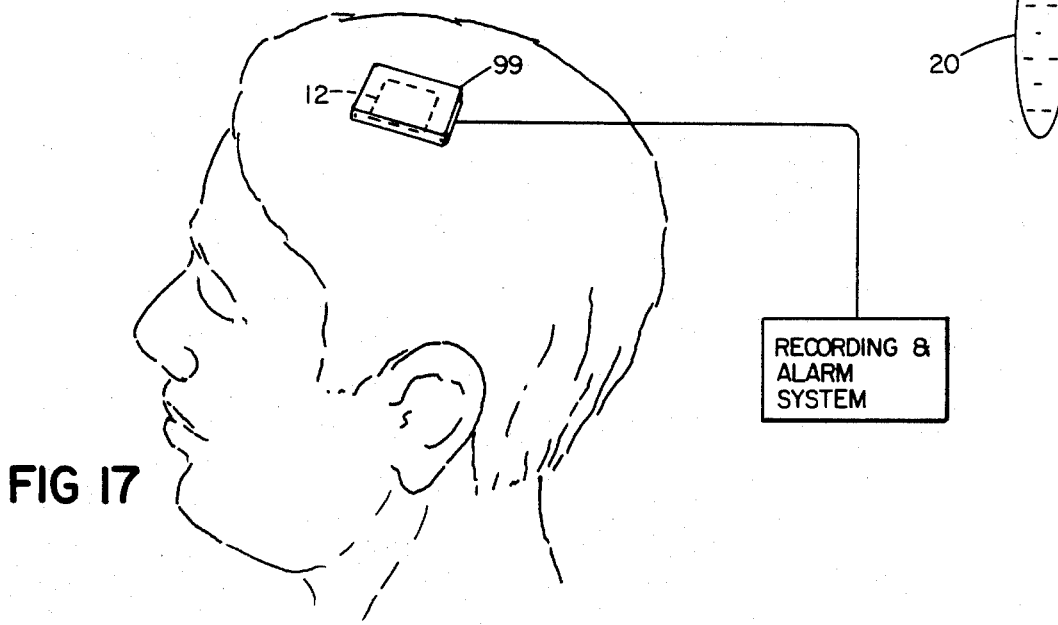
FIG. 17 is a diagrammatic illustration of the implanted manometer and an external magnetic probe for providing recording capabilities.

Other embodiments of the invention are within the scope of the following claims. For example, different physiopathological parameters than intracranial pressure could be measured; e.g., sugar levels in treatment of diabetes, venous pressure, and parameters generated by an implanted pacemaker; altogether different mechanisms for translating variation in a physiopathological parameter into a change in the orientation (e.g., rotation or translation) of a magnetic field could be employed; as shown in FIG. 17, means could be provided for making automatic measurements of the orientation of the magnetic field (e.g., by using an external detection device 99 containing a magnetic probe or a plurality of Hall effect cells to detect the angular orientation of disk 28), thereby providing an electrical output for continuous monitoring of a patient; other magnetic elements than the disks disclosed could be provided in the implanted device; a plurality of measurements could be made to transfer several digits of a numerical value (e.g., by using a plurality of disks 28, one for each digit in a three digit measured value); and a magnetometer capable of indicating magnetic polarity could be used as a viewer.

What is claimed is:

1. The method of transmitting from within the body information regarding an internal parameter, comprising the steps of
   surgically implanting a device containing means for generating a magnetic field having a spatial orientation with respect to said device that is influenced by changes in said parameter, and
   using an external detection element to detect the spatial orientation of said field with respect to said device, to thereby detect said changes in said parameter.

2. The method of claim 1 wherein said parameter is an intracranial pressure.

3. The method of claim 2 wherein said implanted device comprises a manometer including a diaphragm or bellows and means for translating movement of said diaphragm or bellows into rotation of a member supporting one or more magnets.

4. The method of claim 2 wherein said parameter is the pressure difference across a cerebrospinal fluid shunt valve and wherein said implanted device is a manometer connected in parallel with an implanted said shunt valve.

5. The method of claim 4 further comprising implanting a valve or valves capable of changing connections to said manometer from a first state in which a first port of said manometer is connected upstream of said valve and a second port is connected downstream thereof to a second state in which both said first and second ports are connected upstream of said valve, and wherein said method comprises actuating said valves so as to place said connections in said second state to zero said manometer and then to place said connections in said first state to measure the pressure difference across said valve.

6. The method of claim 4 wherein the pressure reference for said manometer is an atmospheric pressure.

7. The method of claim 6 wherein said atmospheric pressure is provided by a fluid-filled bladder placed subcutaneously.

8. The method of claim 1 wherein said implanted device comprises one or more permanent magnets.

9. The method of claim 8 wherein said permanent magnets are supported on a member that is adapted to move under the influence of said parameter.

10. The method of claim 9 wherein said member is adapted to rotate about an axis.

11. The method of claim 10 wherein said member comprises a magnetic alloy disk on which are impressed permanent magnetic regions forming said magnets.

12. The method of claim 11 wherein the boundary between polar regions of at least one said magnet is adapted to define said orientation.

13. The method of claim 12 wherein the boundary between polar regions has the form of an image for viewing by said detection element.

14. The method of claim 1 wherein said detection element comprises a viewer having means for providing a displey indicative of said orientation.

15. The method of claim 14 wherein said viewer comprises means for displaying an image corresponding to the spatial distribution of said magnetic field.

16. The method of claim 15 wherein said means for displaying comprises a multiplicity of movable ferromgnetic particles.

17. The method of claim 16 wherein said means for displaying comprises a weakly-ferromagnetic crystal suspension.

18. The method of claim 15 wherein said implanted device includes a rotatable member with at least two permanent magnetic regions, said orientation is a rotational change in the position of said field, said spatial distribution is adapted to provide an indication of the center of said rotation, and a pointer means is provided on said viewer that is adapted to be aligned with said indication of the center and adapted to be rotated into a preselected orientation with said distribution so that a measurement can be made after said alignment and rotation by comparing the position of said pointer means with a scale on said viewer.

19. The method of claim 14 wherein said viewer comprises a magnetic element adapted to align itself in said field in a predetermined relationship to said orientation.

20. The method of claim 19 wherein said magnetic element comprises a rotatable permanent magnet such as a compass needle.

21. The method of claim 14 wherein said implanted device includes at least two permanent magnets having a boundary between adjoining polar regions that defines an image for viewing by said viewer.

22. The method of claim 21 wherein said viewer comprises a scale for directly reading values of said parameter and said image has the shape of a pointing means for indicating a position along said scale.

23. The method of claim 22 wherein said viewer comprises a ferromagnetic suspension with a generally circular display area and said scale comprises markings around the periphery of said circular display area and wherein said implanted device has a rotatable element on which said magnets are arranged to define an image in the form of a pointer with a center of rotation that is aligned with the center of said display area when measurements are made.

24. The method of claim 23 wherein said pointer image has asymmetry so that a full 360° rotation may be used for reading measurements.

25. The method of claim 21 wherein said at least two permanent magnets have strengths sufficiently similar and shapes adapted to provide said image in generally undistorted form at varying separations between said implanted device and said viewer.

26. The method of claim 14 wherein said viewer comprises a magnetometer adapted to indicate magnetic polarity.

27. The method of claim 1 wherein said step of using a detection element comprises using a means for generating an electrical signal representative of said orientation, and further comprising the step of continuously monitoring said parameter by detecting whether said electrical signal remains in a desired range of values.

28. The method of claim 27 wherein said step of using a means for generating a electrical signal comprises using Hall effect cells or a magnetometer adapted to indicate magnetic polarity.

29. The method of claim 1, wherein said parameter is a physiopathological parameter being measured by said surgically-implanted device.

30. The method of claim 1, wherein said magnetic field generating means within said device is a permanent magnet and said magnet is adapted to move in dependent response to changes in said internal parameter, to thereby produce said variation in the spatial orientation of said magnetic field.

31. A surgically-implantable device for use as part of apparatus for transmitting from within the body information regarding an internal parameter, said device containing means for generating a magnetic field having a spatial orientation with respect to said device that is influenced by changes in said parameter, said means and device being adapted so that changes in the spatial orientation of said magnetic field with respect to said device are detectable outside of the body.

32. Apparatus for transmitting from within the body information regarding an internal parameter, comprising
a surgically-implantable device containing means for generating a magnetic field having a spatial orientation with respect to said device that is influenced by changes in said parameter, said means and device being adapted so that changes in the spatial orientation of said magnetic field with respect to said device are detectable outside of the body, and
detection apparatus comprising a detection element with means for detecting the spatial orientation of said magnetic field with respect to said device after said device has been surgically implanted.

33. Apparatus of claim 32 wherein said parameter is an intracranial pressure.

34. The apparatus of claim 33 wherein said implantation device comprises a manometer including a diaphragm or bellows and means for translating movement of said diaphragm or bellows into rotation of a member supporting one or more magnets.

35. The apparatus 33 wherein said parameter is the pressure difference across a cerebrospinal fluid shunt valve and wherein said implantion is a manometer connected in parallel with an implantion device said shunt valve.

36. The apparatus of claim 32 wherein said implantable device comprises one or more permanent magnets.

37. The apparatus of claim 42 wherein said permanent magnets are supported on a member that is adapted to move under the influence of said parameter.

38. The apparatus of claim 37 wherein said member is adapted to rotate about an axis.

39. The apparatus of claim 38 wherein said member comprises a magnetic alloy disk on which are impressed permanent magnetic regions forming said magnets.

40. The apparatus of claim 39 wherein the boundary between polar regions of at least one said magnet is adapted to define said orientation.

41. The apparatus of claim 40 wherein the boundary between polar regions has the form of an image for viewing by said detection element.

42. The apparatus of claim 32 wherein said detection element comprises a viewer having means for providing a display indicative of said orientation.

43. The apparatus of claim 42 wherein said viewer comprises means for displaying an image corresponding to the spatial distribution of said magnetic field.

44. The apparatus of claim 43 wherein said means for displaying comprises a multiplicity of movable ferromagnetic particles.

45. The apparatus of claim 44 wherein said means for displaying comprises a weakly-ferromagnetic crystal suspension.

46. The apparatus of claim 43 wherein said implantable device includes a rotatable member with at least two permanent magnetic regions, said orientation is a rotational change in the position of said field, said spatial distribution is adapted to provide an indication of the center of said rotation, and a pointer means is provided on said viewer that is adapted to be aligned with said indication of the center and adapted to be rotated into a preselected orientation with said distribution so that a measurement can be made after said alignment and rotation by comparing the position of said pointer means with a scale on said viewer.

47. The apparatus of claim 42 wherein said viewer comprises a magnetic element adapted to align itself in said field in a predetermined relationship to said orientation.

48. The apparatus of claim 47 wherein said magnetic element comprises a rotatable permanent magnet such as a compass needle.

49. The apparatus of claim 42 wherein said implantable device includes at least two permanent magnets having a boundary between adjoining polar regions that defines an image for viewing by said viewer.

50. The apparatus of claim 49 wherein said viewer comprises a scale for directly reading values of said parameter and said image has the shape of a pointing means for indicating a position along said scale.

51. The apparatus of claim 50 wherein said viewer comprises a ferromagnetic suspension with a generally circular display area and said scale comprises markings around the periphery of said circular display area and wherein said implantable device has a rotatable element on which said magnets are arranged to define an image in the form of a pointer with a center of rotation that is aligned with the center of said display area when measurements are made.

52. The apparatus of claim 51 wherein said pointer image has asymmetry so that a full 360° rotation may be used for reading measurements.

53. The apparatus of claim 49 wherein said at least two permanent magnets have strengths sufficiently similar and shapes adapted to provide said image in generally undistorted form at varying separations between said implantable device and said viewer.

54. The apparatus of claim 42 wherein said detection element comprises means for generating an electrical signal representative of said orientation, magnetic polarity being indicated by Hall effect cells or a magnetometer.

55. The apparatus of claim 31 or 32 wherein said parameter is a physiopathological parameter being measured by said surgically-implantable device.

56. The apparatus of claim 31 or 32 wherein said magnetic field generating means within said device is a permanent magnet and said magnet is adapted to move in dependent response to changes in said internal parameter, to thereby produce said variation in the spatial orientation of said magnetic field.

57. The method of measuring cerebrospinal fluid pressure comprising the steps of
implanting a shunt valve in a conduit connecting the cerebral ventricle to a drainage site, and
implanting a manometer with first and second pressure ports connected in parallel with said shunt valve so that said first pressure port of said manometer is connected upstream of said valve and said second pressure port is connected downstream of said valve, thereby providing that said manometer measures the pressure difference across said valve.

58. The method of claim 57 wherein said method further comprises implanting a valve or valves capable of changing the connections to said manometer from a first state in which said first port of said manometer is connected upstream of said valve and said second port is connected downstream thereof to a second state in which both said first and second ports are connected upstream of said valve, and wherein said method comprises actuating said valves so as to place said connections in said second state to zero said manometer and then to place said connections in said first state to measure the pressure difference across said valve.

59. The method of claim 25 wherein the pressure reference for said manometer is an atmospheric pressure.

60. The method of claim 59 wherein said atmospheric pressure is provided by a fluid-filled bladder placed subcutaneously.

61. The method of claim 57 wherein the pressure reference for said manometer is the right atrium of the heart.

* * * * *